United States Patent [19]
Blanco et al.

[11] Patent Number: 4,667,665
[45] Date of Patent: May 26, 1987

[54] NON-OCCLUSIVE BURN AND TRAUMA DRESSING

[75] Inventors: Carlos Blanco, Tarrytown; Anthony Siragusa, West Nyack, both of N.Y.

[73] Assignee: Colin O'D. Offenhartz, Chappaqua, N.Y.

[21] Appl. No.: 830,902

[22] Filed: Feb. 18, 1986

Related U.S. Application Data

[63] Continuation of Ser. No. 641,325, Aug. 16, 1984.

[51] Int. Cl.$^4$ ............................................. A61L 15/00
[52] U.S. Cl. ..................... 128/156; 604/378
[58] Field of Search ................ 128/156, 155; 604/378, 604/289

[56] References Cited

U.S. PATENT DOCUMENTS

| | | | |
|---|---|---|---|
| 2,877,765 | 3/1959 | Bunyan | 128/156 |
| 2,923,298 | 2/1960 | Dockstader et al. | 128/296 |
| 3,221,738 | 12/1965 | Ekberg et al. | 128/287 |
| 3,336,923 | 8/1967 | Devaud | 128/156 |
| 3,416,523 | 12/1968 | Yeremian | 128/156 |
| 3,416,526 | 12/1968 | Yeremian | 128/156 |
| 3,434,472 | 3/1969 | Herniman | 128/156 |
| 3,446,208 | 5/1969 | Fukuda | 128/156 |
| 3,545,442 | 12/1970 | Wieber | 128/296 |
| 3,602,220 | 8/1971 | Bunyan | 128/156 |
| 3,703,897 | 11/1972 | Mack et al. | 128/156 |
| 3,815,602 | 6/1974 | Johns et al. | 128/287 |
| 3,838,692 | 10/1974 | Levesque | 128/284 |
| 3,871,378 | 3/1975 | Duncan et al. | 128/290 |
| 3,888,248 | 6/1975 | Moore et al. | 604/369 |
| 3,930,498 | 1/1976 | Monnet et al. | 128/156 |
| 3,965,906 | 6/1976 | Karami | 128/287 |
| 3,967,623 | 7/1976 | Butterworth et al. | 128/287 |
| 4,077,410 | 3/1978 | Butterworth et al. | 128/287 |
| 4,090,897 | 5/1978 | Minick | 156/73.1 |
| 4,196,562 | 4/1980 | Hirschman | |
| 4,203,435 | 5/1980 | Krull | 128/156 |
| 4,289,125 | 9/1981 | Hung | 128/156 |
| 4,321,924 | 3/1982 | Ahr | 128/287 |
| 4,360,015 | 11/1982 | Mayer | 128/156 |
| 4,373,979 | 2/1983 | Planeta | 156/73.1 |
| 4,404,052 | 9/1983 | Persson et al. | 156/73.1 |
| 4,541,426 | 9/1985 | Webster | 128/156 |

*Primary Examiner*—John D. Yasko
*Attorney, Agent, or Firm*—Gottlieb, Rackman, and Reisman

[57] ABSTRACT

A non-medicated dressing having a non-adherent permeable outer casing and a multi-strata absorbent interior composition. The outer casing of the dressing includes a skin contacting layer formed of superimposed strata of perforated high density polyethylene film. An exterior layer of the casing includes a lamination of permeable polyethylene film and a layer of absorptive material, the combination having a density and thickness specifications which maintain the structural integrity of the dressing. The dressing has a soft and cushioned exterior finish which conforms to the body contour. The dressing is manufactured in accordance wtih a method which employs a combined cutting and ultrasonic sealing apparatus.

11 Claims, 8 Drawing Figures

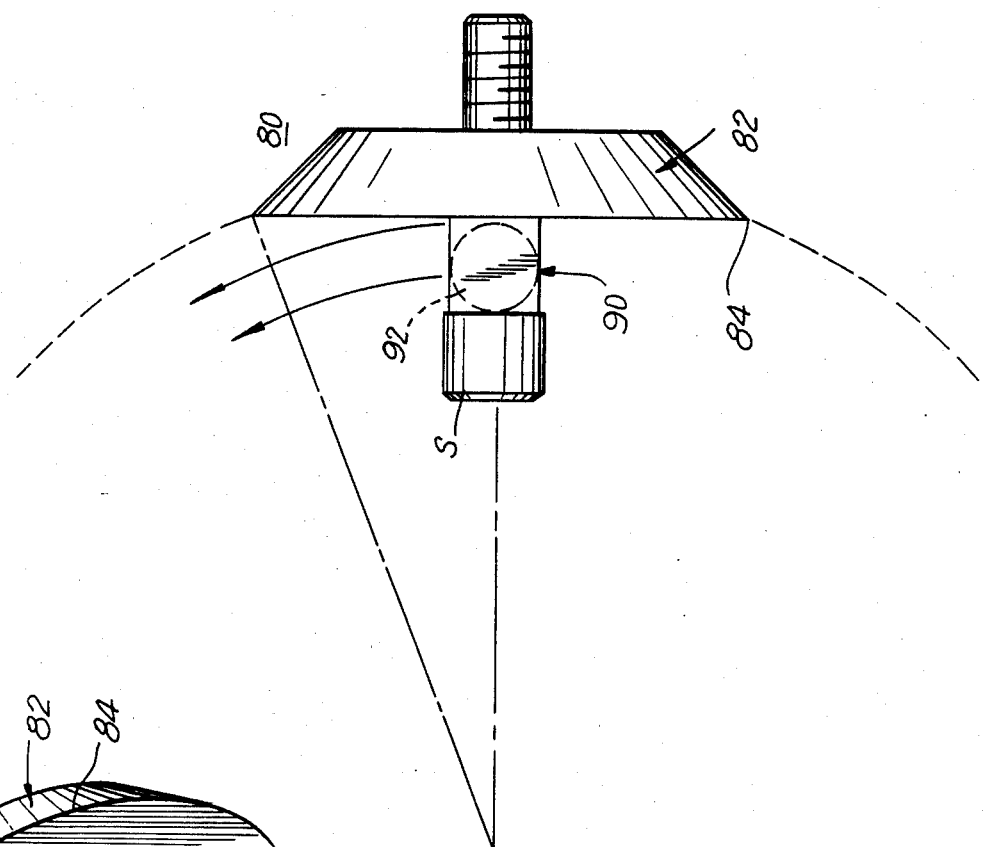
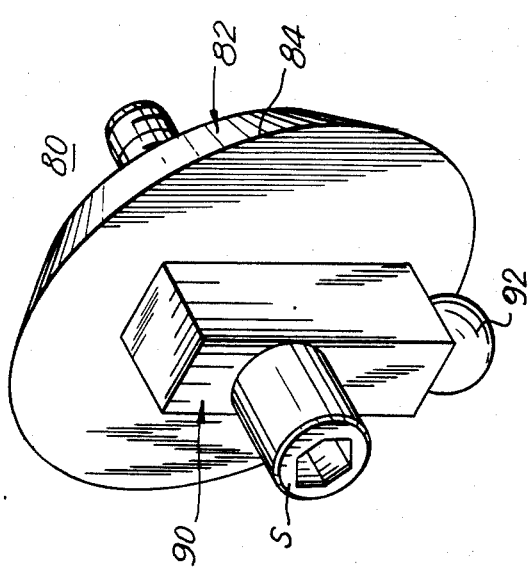
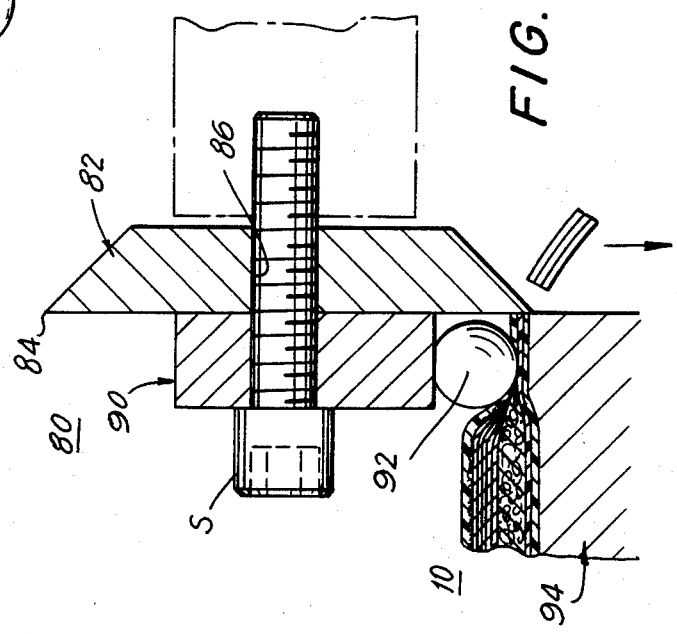

NON-OCCLUSIVE BURN AND TRAUMA DRESSING

This application is a continuation of application Ser. No. 641,325 filed 08/16/84.

DESCRIPTION

1. Technical Field

This invention relates generally to non-medicated dressings for care of bodily wounds, burns and the aftercare of surgical incisions. More particularly, the invention is concerned with a dressing which has application for use either separately or with topical medications in a sterile environment whenever a lint free, non-adherent, non-occlusive, highly absorbent dressing is indicated. The dressing conforms to the anatomy of surgical or other wound sites to obtain effective absorption of body exudates and has the capacity to transmit fluids and topical medications to the skin surface.

2. Background Art

Surgical and wound dressings which absorb bodily exudates and maintain fluids and topical medications at the skin surface for use in the treatment of burn patients are generally well known in the medical arts and in the medical industry. Sterile dressings of this type are necessary in order to facilitate examination of wounds and dressing changes, and maintain an incision free of lint or other contaminants which can lead to the complication of granulomas. Additionally, non-adherence to a wound or incision is necessary in order to minimize pain associated with the removal and replacement of dressings, as well as wound trauma and its associated risks of infection and delayed healing.

By way of example, the treatment of burns involves the periodic exuding of bodily liquids such as lymph, and blood. In order to treat such symptoms, it is necessary to employ a bandage which is non-adherent and highly absorbent to effect dispersion of bodily discharges. Such dressings must also have the capacity to absorb fluids and medicaments in order to guard against infection and dehydration of the patient.

Although the medical art has recognized the need for non-adherent dressings having absorptive characteristics, the art has not provided a dressing which has proved entirely satisfactory in practice. In general, known dressings have not been characterized by sufficient pliability to facilitate conforming placement of the dressing on the body.

In one prior art approach, represented by U.S. Pat. No. 4,360,015 to Mayer, a dressing is disclosed which includes a non-adherent permeable polyethylene outer-layer which contacts the wound surface, and an exterior moisture-resistant barrier on its opposing side, both enclosing interior absorbent layers fabricated of cellulose and hydropilic fiber groupings. In order to maintain the structural integrity of the dressing and effect uniform absorption of body exudates, a grid member is joined and positioned between the cellulosic layer and hydrophilic fibers. This grid member, which is nonabsorbent, limits the flexibility, pliability, and effectiveness of the dressing.

Another prior art dressing characterized by a grid structure is disclosed in U.S. Pat. No. 3,888,248 to Moore, directed to an abdominal pad in which the application side or covering includes superposed layers of tear resistant grid material, and a layer of polyethylene. Again, the grid structure limits the pliability of the dressing.

Other teachings of the art focus attention on the need to provide a non-adherent permeable wound contacting layer of material which has sufficient capillary characteristics to remove body exudates from the skin surface effectively. In this connection, reference may be had to U.S. Pat. Nos. 2,923,298 to Dockstader and 2,877,765 to Bunyan. Absent in these teachings and the art is a dressing which may be conformingly positioned at a wound or surgical incision in order to permit optimum absorption of body exudates while providing a moist environment at a wound site.

Accordingly, it is the broad object of the present invention to provide an improved burn and trauma dressing of integral design which is non-adherent and has high absorption characteristics.

Another object of the present invention is to provide an improved dressing which by its design conforms readily to the body contour in order to facilitate its application to the body, removal and repositioning for examination of a wound or incision.

Yet another object of the present invention is to provide an economical method for the manufacture of burn and trauma dressings to prescribed dimensional configurations.

DISCLOSURE OF THE INVENTION

In the present invention, these purposes, as well as others which will be apparent, are achieved generally by providing a non-occlusive burn and trauma dressing having a non-adherent permeable outer casing and a multi-strata absorbent interior composition. The burn and trauma dressing by reasons of its material composition has a soft and cushioned exterior finish which conforms readily to the body contour for effective absorption of exudates and introduction of fluids and medicaments to the skin surface. The outer casing of the dressing includes a non-adherent skin contacting layer formed of superimposed strata of perforated high density polyethylene film. The strata are orientated in angularly offset relation to minimize spacing between perforations, thereby providing strength to the dressing and eliminating the passage of absorptive materials from the interior of the dressing to the skin surface. An exterior layer of the casing includes a lamination of permeable high density polyethylene film and a layer of absorptive material, the combination having a density and thickness sufficient to maintain the structural integrity of the dressing when it is saturated with body exudates, topical medications and fluids. The dressing is provided as an integral closed unit with the outer casing sealed at peripheral edges enclosing the interior layers of absorbent materials.

In accordance with a manufacturing method of the invention, a combined cutting and ultrasonic sealing apparatus is employed which facilitates economic fabrication of dressings to selected configurations. The apparatus includes a cutting edge and bearing ball which simultaneously contact the peripheral edge of the dressing during cutting operations. An ultrasonic energy source coacts with the bearing to seal the edges of the dressing.

BRIEF DESCRIPTION OF THE DRAWINGS

FIG. 6 is a perspective view of a sealing and cutting apparatus employed to cut the edges of the dressing and form a sealed peripheral edge;

FIG. 7 is a plan view of the cutting apparatus generally illustrating its radius of rotation on a curved edge of the dressing, indicating the motion path of a fixed bearing ball employed in connection with an ultrasonic sealing process for forming the dressing edges; and FIG. 8 is a front view of the cutting apparatus positioned at of the edge of the dressing, illustrating the manner in which the apparatus coacts with an ultrasonic source to seal and cut the dressing edges.

BEST MODE FOR CARRYING OUT THE INVENTION

Figure 1:
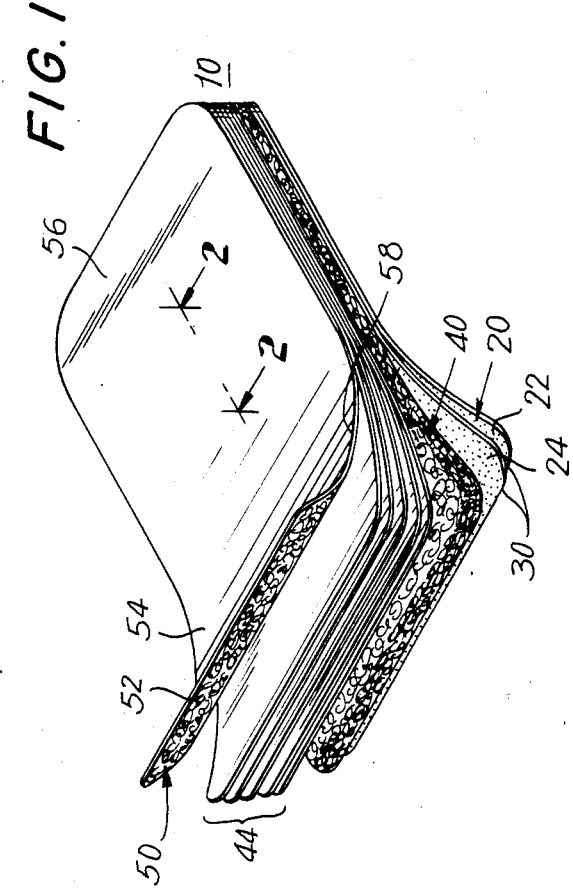
FIG. 1 is a perspective view of the burn and trauma dressing of the present invention in which component layers of the dressing have been peeled away for clarity of illustration.

Referring now to the drawings and, more particularly, FIGS. 1-5 thereof, there is illustrated a non-occlusive burn and trauma dressing according to the present invention, generally designated 10, including a non-adhering outer casing formed of a skin contacting layer 20, an absorbent multi-strata interior layer 40, and an exterior permeable layer 50.

The skin contacting layer of the dressing 20 has a substantially planar section 26 which includes a plurality of perforations 28 and terminates at a peripherally extending edge 30. Skin contacting layer 20 is preferably fabricated of a material which is non-adherent and highly pliable, so that the dressing conforms to the body contour facilitating its placement and removal for examination purposes without adherence to the skin with associated complications and body trauma. Perforation spaces 28 in the contacting dressing layer are preferably dimensioned to prevent passage of lint and other absorbent fibers from the interior of the dressing to the skin surface, which leads to increased risk of infection, delayed healing and the complication of granulomas.

Figure 2:
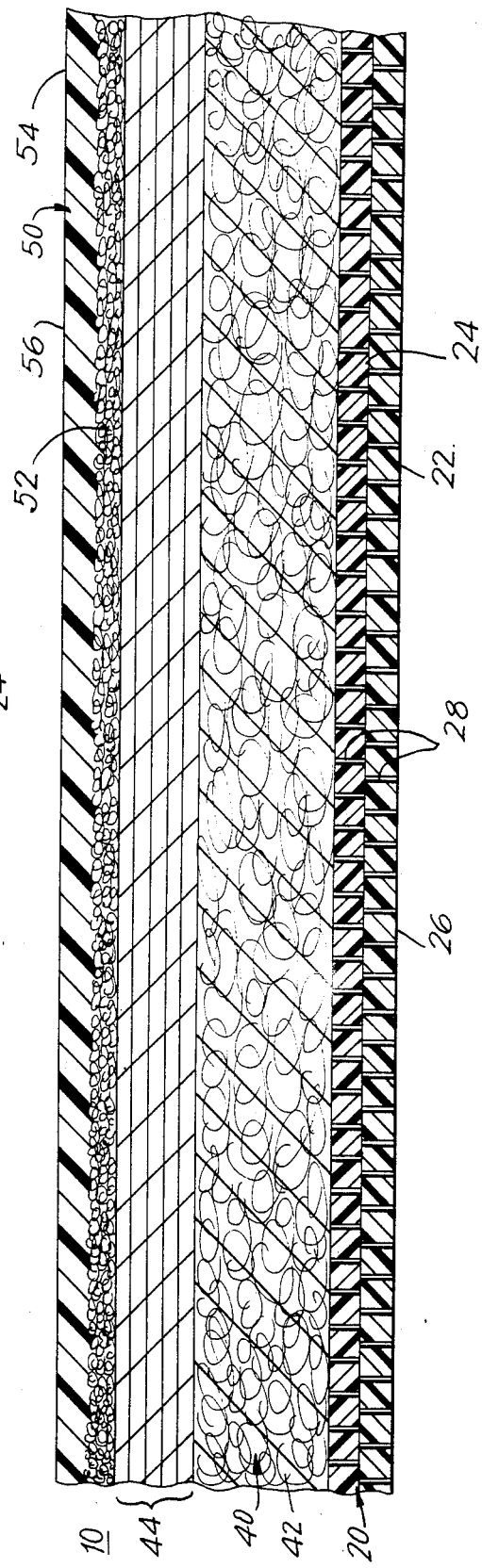
FIG. 2 is an enlarged rectangular cross-sectional view through the body of the dressing, taken along the plane defined by line 2—2 of FIG. 1.

In the preferred embodiment, wound contacting layer 20 is formed of two superimposed strata of perforated polyethylene film 22, 24 each having a thickness of 4.3 mils, a density of 15 pounds per cubic feet or greater, and perforation spacing of 9 dots per centimeter. As best shown in FIG. 2, the polyethylene film strata 22, 24 are orientated in angularly offset relation in order to minimize the effective spacing between strata perforations. A suitable perforated polyethylene film for fabrication of the dressing is commercially available under the trademark DELNET, manufactured by Hercules Incorporated, 910 Market Street, Wilmington, De. 19899 DELNET polyethylene product designation P530 has a perforation density of 34% which yields a permeable non-adherent characteristic when employed in fabrication of the dressing 10 of the present invention.

The absorbent interior layer 40, which may be fabricated of strata of cellulose and blended polyester and rayon materials, is encased between the wound contacting and exterior layers 20, 50 of the dressing. The absorbent interior layer 40 retains exudates from the body which permeate through the skin contacting layer 20. In order to provide a cushioned dressing 10 and maximal comfort to the wearer of the dressing, the absorbent interior layer 40 should have excellent absorbency and bulk so that exudates permeate fully through the skin contacting layer 20, while maintaining the exterior skin contacting surfaces of the dressing 10 free from discharge products. To this end, the absorbent layer 40 has a homogeneous material content which is loosely compacted within the dressing 10.

Figure 4:
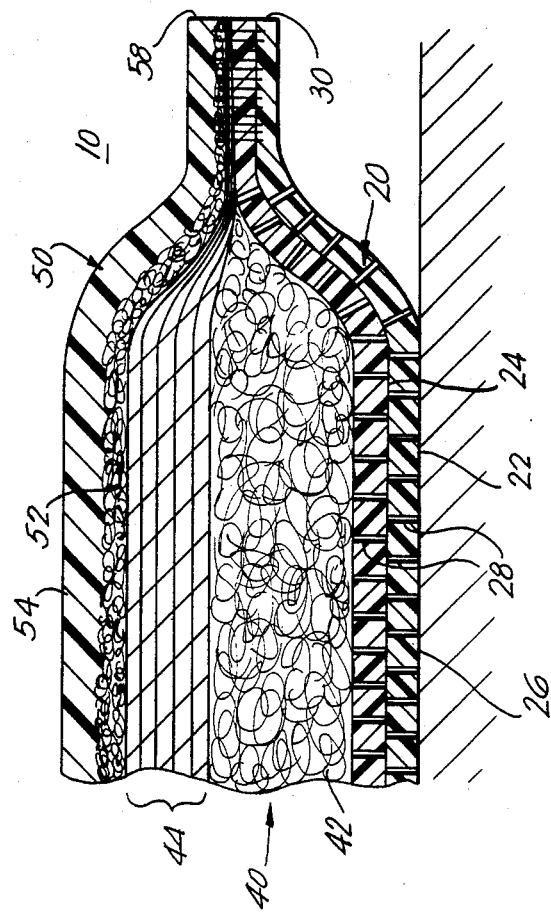
FIG. 4 is an enlarged and broken away cross-sectional view of the dressing taken along the line 4—4 of FIG. 3 positioned above the skin line, showing its multiple layers and sealed peripheral edge.
Figure 3:
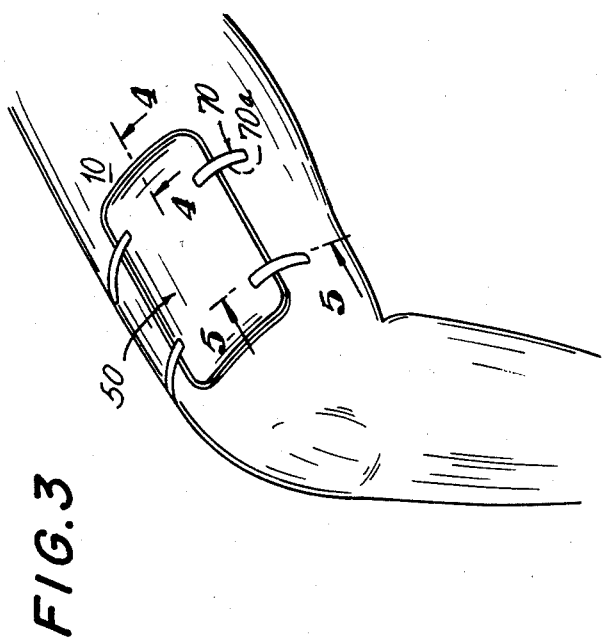
FIG. 3 is a top elevational view of the dressing applied and fastened to the thigh of a patient by adhesive tapes.
Figure 5:
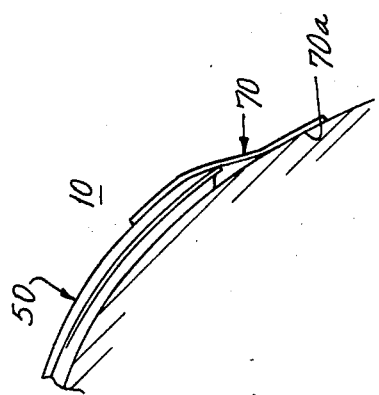
FIG. 5 is a partially broken away view of the dressing taken along the line of 5—5 of FIG. 3 showing the manner in which fastening tapes secure the dressing to the skin.

In the preferred embodiment of the invention the absorbent interior layer 40 includes a blended polyester and rayon stratum 42 adjacent the skin contacting layer 20 having a composition of 70% polyester and 30% rayon, on which is superimposed five cellulose strata 44, see FIGS. 2 and 4. Blended polyester and rayon stratum and cellulose strata materials suitable for fabrication of the dressing 10 are commercially available from Acme/Chaston, Division of National Patent Development Corp., P.O. Box 425, Lake Road, Dayville, Conn. 06241. Characteristics of these materials are as follows:

| Acme/Chaston Blended Polyester and Rayon | |
| --- | --- |
| Composition | 70% polyester, 30% rayon |
| Thickness | 0.5 inches |
| Density | 194 grams per square yard |
| Acme/Chaston Cellulose Fiber | |
| Composition | Bleached white sulphide creped wadding |
| Basic Weight | .162 lb per square yard ±10% (per Strata) |
| Thickness | 13.2 mils per strata |

The exterior layer 50 of the dressing which may have the same dimensions as that of the skin contacting layer 20, includes a substantially planar portion 56 which terminates at a peripherally extending edge 58. In order to permit application of liquid topical therapy to a wound or surgical incision, the exterior layer 50 is preferably permeable. The exterior layer 50 is also provided with a density and thickness sufficient to maintain the structural integrity of the dressing 10 when it is satuated with bodily exudates, topical medications and fluids.

In the preferred embodiment of the invention, the exterior layer 50 includes a lamination of permeable high density perforated polyethylene film 54 and an absorbent blend of 80% polyester and 20% rayon 52. DELNET polyethylene film 54 of the type employed in fabrication of the skin contacting layer 20 is suitable for use in the exterior layer. The blended polyester and rayon component 52 of the exterior layer 50 should have a thickness in the range of 30 to 35 mils, weight of 4.5±10% oz. per square yard, and permeability rate of 200±15 cubic feet per minute of airflow. Style 319-D polyester and rayon blend manufactured by Malik Industries Inc., Malvern, Pa. 19355 has been found effective for purposes of the present invention. Style 319-D blended polyester and rayon has a water holding capacity of 9 to 10 times per gram of sub-strata material and density of 15 pounds per cubic feet. Advantageously, employment of a lamination of permeable polyethylene film 54 and blended polyester and rayon 52 having a thickness in the range of 35 to 40 mils, in combination with skin contacting and absorbent layers 20, 40 imparts structural integrity to the dressing 10 when satuated with fluids and exudates.

It will be appreciated that advantage is obtained by maintaining flexibility in the dressing to permitits conforming placement on the body, while avoiding clumping of interior absorbing materials of the dressing which hinders uniform absorption of exudates and fluids. Moreover, this result is obtained without employment of inflexible grid-like structures of the prior art, see U.S. Pat. No. 4,360,015 to Mayer.

Referring to FIG. 4, the skin contacting and exterior layers 20, 50 of the dressing are sealed at their respective peripheral edges 30, 58 by application of ultrasonic energy. As will be described hereinafter, the present invention employs a sealing and cutting apparatus and method which facilitates economical trimming and finishing of the dressing 10 to desired dimensions. The resulting dressing 10 has a soft rounded peripheral edge which reduces the risk of injury to the wound.

The burn and trauma dressing 10 is secured in conforming relation to the body by a tape fastening means which includes conventional pressure-sensitive tapes 70 which may be provided as separate components for use with the dressing 10. The tapes 70, shown in FIGS. 3 and 5, adhesively contact the exterior layer 50 of the dressing and the skin surface. The adhesive tape 70 includes an adhering surface 70a and peel-off non-adhesive protective coverings (not shown). The coverings facilitate handling of the adhesive tapes 70 prior to use and also prevent the tapes from drying out or otherwise deteriorating.

Adhesive tapes 70 may be fabricated of conventional materials which are hypoallergenic and adhere securely to the skin with minimal skin irritation.

METHOD OF MANUFACTURING THE BURN AND TRAUMA DRESSING

Conventional manufacturing techniques are employed in fabrication of the dressing 10 of the present invention. As known to those in the art, it is commonplace to advance webs of the various strata of material to cutting and trimming stations and assembling component layers of the dressing to form an integral product.

In the manufacture of the dressing of the present invention, a cutting and ultrasonic sealing apparatus 80, illustrated in FIGS. 6-8, is employed to obtain economies and a dressing finish having a soft edge and rounded corners. Apart from facilitating the economic fabrication of dressings of selected dimensions, the rounded edge finish diminishes the risk of injury to the wound, and pain which can be caused by abrasive contact of the dressing to the skin surface.

The cutting instrument employed in the method of the invention includes a circular wheel 82 which has a peripherally extending cutting edge 84 and a central threaded aperture 86. A fitting 90 including a pressure means at its base end is connected to the circular cutting disk through aperture 86 by conventional screw S which extends through the fitting and aperture in the disk.

The pressure means of the cutting apparatus includes a bearing ball 92 which, as shown in FIG. 8, is oriented adjacent the cutting edge 84 of wheel 82 a spaced distance from the peripheral cutting edge 84. In application of the device, the cutting edge 12 and bearing ball 92 simultaneously contact the peripheral edges of the dressing 10, which rest on an ultrasonic source 94. Manufacturing economies are effected by simultaneously applying ultrasonic energy at 94 during cutting and trimming operations with the cutting apparatus. In this manner, the bearing ball 92 coacts with the ultrasonic energy source to seal the peripheral edges 30, 58 of the dressing 10 simultaneously with the cutting operation.

With reference to FIG. 7, it will be seen that the cutting and sealing apparatus 80 may be advanced in a circular motion to obtain the desired rounded edge configuration of the dressing of this invention. Additionally, it will be observed that the fitting 90 with integral bearing ball 92 is universally positionable through 360° of circumference of the cutting edge 84 for selective placement. This feature effects further manufacturing economies by lengthening the effective life of the cutting edge 84. As sections of the outer circumference of the cutting edge 84 become dulled in the manufacturing process, the fitting 90 may be rotated a spaced distance relative to the wheel 82 by adjusting screw S in order to provide a new cutting edge for further operations, without requiring the physical removal of the cutting edge, as is often needed when using blades of the type employed in known manufacturing methods.

From the foregoing, it will be appreciated that the present invention provides a burn and trauma dressing 10 which overcomes the difficulties of prior art arrangements and achieves the objects stated heretofore.

In particular, the present invention provides a dressing 10 including improved design features which provide a cushioned, soft, and pliable dressing which conforms readily to the body contour facilitating its positioning in close-fitting relation to the body. The dressing is non-adherent, and has high absorption characteristics which permit its use for care of burns as well as in the care of post-surgical incisions.

More particularly, the dressing 10 includes a non-adhering skin contacting layer 20 formed of superimposed strata of polyethylene film 22, 24 which are non-adhering to skin surfaces and eliminate passage of lint and other materials from the interior of the dressing to the skin surface. An interior absorbent layer 40 effects a uniform dispersal of body exudates and fluids, and an exterior permeable layer 50, including a lamination of polyethylene film 54 and blended polyester and rayon 52, permits introduction of fluids and medicaments for treatment of the skin surface. In combination with skin contacting and absorbent layers 20 and 40, exterior layer 50 provides structural strength and integrity to the dressing. Still further advantage is obtained in the dressing by employing a sealing and cutting apparatus and ultrasonic method to seal and cut the peripheral dressing edges 30, 58, providing rounded soft and non-abrasive edges for the dressing and economies in the manufacturing process.

Numerous modifications are possible in light of the disclosure. By way of example, there is disclosed an absorbent interior layer 40 fabricated of cellulose strata 44 and a blended polyester and rayon stratum 42. Other absorbent materials may be employed provided they have the absorption, density and bulk specifications of the disclosed dressing. For example, the blended polyester and rayon stratum may be replaced with cotton and rayon stratum. In a similar manner, although ultrasonic sealing of the peripheral edges of the skin contacting and exterior dressing layers is preferred, other conventional sealing processes may be employed. It is to be understood, therefore, that the above-described embodiments are merely illustrative and other embodiments may be devised by those skilled in the art, without departing from the spirit or scope of the present invention, as set forth in the appended claims.

We claim:

1. A non-occlusive dressing adapted for conforming arrangement on a person's body contour, said dressing comprising:
    (a) a skin contacting layer comprising two superimposed strata of a film, said film being made of a non-adherent material and provided with a plurality of perforations;
    (b) an absorbent interior layer comprising a homogeneous absorbent material loosely compacted within the dressing, said material substantially retaining exudates from the body which permeate through said skin contacting layer, said perforations of said skin contacting layer dimensioned to eliminate passage of said absorbent material from said interior layer to a patient's skin; and
    (c) an exterior layer comprising a film member, said skin contacting layer and said exterior layer being positioned in overlying and sealing relation with respect to said interior layer to form an integral dressing, the exterior layer having sufficient thickness to maintain the structural integrity of the dressing when the absorbent interior layer is saturated with exudates, topical medications and fluids.

2. A non-occlusive dressing according to claim 1, wherein said skin contacting and exterior layers have substantially planar configurations and substantially opposing peripherally extending edge portions, the skin contacting and exterior layers being sealed to each other at said peripheral edges.

3. A non-occlusive dressing according to claim 1, wherein said skin contacting layer performance are dimensioned and sufficiently dense to render said film permeable to said body exudates.

4. A non-occlusive dressing according to claim 2, wherein said exterior layer is permeable to topical medications and fluids applied to the dressing.

5. A non-occlusive dressing according to claim 2, wherein:
    said skin contacting layer comprises two strata of a high-density polyethylene film;
    said absorbent interior layer comprises a layer of cellulose strata and a stratum of blended polyester and rayon; and
    said exterior layer comprises a lamination of a stratum of high-density polyethylene film and a stratum of blended polyester and rayon.

6. A non-occlusive dressing according to claim 5, wherein each of said two strata of polyethylene film of said skin contacting layer has a perforation density of approximately 34%.

7. A non-occlusive dressing according to claim 6, wherein each of said two strata of perforated polyethylene film has an approoximate thickness of 4.3 mils and a density of approximately 15 pounds per cubic foot.

8. A non-occlusive dressing according to claim 5 wherein the absorbent interior layer includes at least five strata of cellulose material having an approximate per strata thickness of 13.2 mils and basic weight of 0.162 lb. per square yard $\pm 10\%$, and the blended polyester and rayon stratum is approximately 70% polyester and 30% rayon and as a thickness of approximately 0.5 inches and density of approximately 194 grams per square yard.

9. A non-occlusive dressing according to claim 5, wherein the exterior layer includes a perforated polyethylene film having a perforation density of approximately 34%, a thickness of approximately 4.3 mils and a density of approximately 15 pounds per cubic foot.

10. A non-occlusive dressing according to claim 5, wherein the blended polyester and rayon component of said exterior layer is approximately 80% polyester and 20% rayon, has a thickness in the range of 30 to 35 mils, a weight of $4.5 \pm 10\%$ oz. per square yard, and a permeability rate of $200 \pm 15$ cubic feet per minute of airflow.

11. A non-occlusive dressing according to claim 2, wherein the peripheral edge portions of said skin contacting and exterior layers are sealed by ultrasonic energy.

* * * * *